United States Patent [19]

Sassiver et al.

[11] 4,341,703
[45] Jul. 27, 1982

[54] 6-[D-α-(COUMARIN-3-CARBOX-AMIDO)ARYLACETAMIDO]-PENICILLANIC ACIDS OR SALTS

[75] Inventors: Martin L. Sassiver, Monsey, N.Y.; James H. Boothe, Montvale, N.J.

[73] Assignee: American Cyanamid Company, Stamford, Conn.

[21] Appl. No.: 304,727

[22] Filed: Sep. 23, 1981

Related U.S. Application Data

[62] Division of Ser. No. 889,675, Mar. 24, 1978, Pat. No. 4,317,774.

[51] Int. Cl.$^3$ .............................................. C07D 499/70
[52] U.S. Cl. ................................. 260/239.1; 424/271
[58] Field of Search ....................... 260/239.1; 424/271

[56] References Cited

U.S. PATENT DOCUMENTS

| | | | |
|---|---|---|---|
| 3,433,784 | 3/1969 | Long et al. | 260/239.1 |
| 3,939,150 | 2/1976 | Murakami et al. | 260/239.1 |
| 3,951,952 | 4/1976 | Hamanaka et al. | 260/239.1 |
| 3,954,734 | 5/1976 | Doub et al. | 260/239.1 |
| 4,005,075 | 1/1977 | Yamada et al. | 260/239.1 |
| 4,303,664 | 12/1981 | Ono et al. | 424/271 |

Primary Examiner—Natalie Trousof
Assistant Examiner—Vera C. Clarke
Attorney, Agent, or Firm—Edward A. Conroy, Jr.

[57] ABSTRACT

This disclosure describes compounds of the class of 6-[D-α-(benzocoumarin-3-carboxamido)-phenylacetamido] penicillanic acids which possess antimicrobial activity.

9 Claims, No Drawings

6-[D-α-(COUMARIN-3-CARBOX-AMIDO)ARYLACETAMIDO]-PENICILLANIC ACIDS OR SALTS

CROSS REFERENCE TO RELATED APPLICATION

This application is a division of our copending application Ser. No. 889,675, filed Mar. 24, 1978, now U.S. Pat. No. 4,317,774.

BRIEF SUMMARY OF THE INVENTION

This invention relates to new derivatives of 6-aminopenicillanic acid and, more particularly, is concerned with novel compounds which may be represented by the following structural formula:

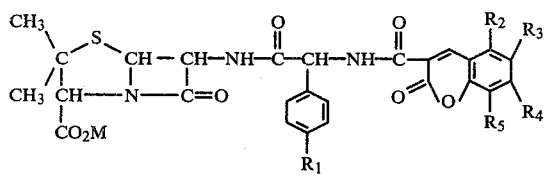

wherein $R_1$ is hydrogen or hydroxy; $R_2$ and $R_3$ taken together, $R_3$ and $R_4$ taken together, and $R_4$ and $R_5$ taken together are each butadienylene; and M is hydrogen or a pharmaceutically acceptable non-toxic cation.

DETAILED DESCRIPTION OF THE INVENTION

The pharmacologically acceptable cations embraced by M in the above general formula include, for example, the non-toxic metal cations such as the sodium ion, potassium ion, calcium ion, magnesium ion, as well as the organic amine cations such as the tri(lower alkyl)amine cations (e.g., triethylamine), procaine, and the like.

The novel compounds of the present invention may be readily prepared by condensing an ampicillin derivative of the formula:

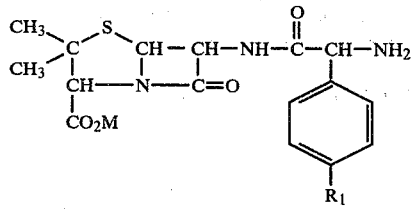

wherein $R_1$ and M are as hereinabove defined with a benzocoumarin-3-carboxylic acid derivative of the formula:

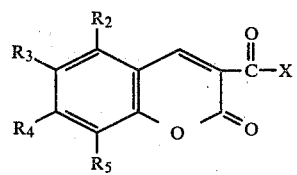

wherein $R_2$, $R_3$, $R_4$ and $R_5$ are as hereinabove defined and X is chloro or bromo as in an acid halide, or the moiety —O—CO—OC$_2$H$_5$ as in a mixed anhydride from ethyl chloroformate, or the moiety —O—C(=N-cyclohexyl)NH-cyclohexyl as in a dicyclohexylcarbodiimide mediated reaction, or an azide function, or an azolide formed from carbonyldiimidazole. This acylation of the ampicillin derivative is best performed in an inert solvent such as tetrahydrofuran, dioxane, methylene chloride or chloroform (or mixtures thereof) at from ice bath temperature (about 0° C.) to room temperature (about 25° C.). The reaction is preferably carried out in the presence of an acid acceptor such as N-methylmorpholine, triethylamine, or soda ash and over a period of a few hours or more. The acylating agents may be prepared by methods well known in the art from the corresponding acid (X is hydroxy). Thus, an acid may be treated with a thionyl halide or oxalyl halide, if desired, in the presence of dimethylformamide, to yield the corresponding acyl halides (X is chloro or bromo), which can be converted to the acyl azides (X is N$_3$) by treatment with sodium azide.

The novel compounds of the present invention are biologically active and have been found to possess antibacterial activity. As indicated, they are useful antimicrobial agents and have broad-spectrum antimicrobial activity in vitro against standard laboratory microorganisms used to screen for activity against pathogens. The antibacterial spectrum of typical compounds of the present invention, representing the concentration required to inhibit the growth of various typical bacteria, was determined in a standard manner by the agar-dilution streak-plate technique. A Steers multiple inocula replicator was employed with incubation at 37° C. for 18 hours in conventional nutrient agar. The results are set forth in Table I below expressed as the minimal inhibitory concentration in micrograms per milliliter.

The invention will be described in conjunction with the following specific examples.

EXAMPLE 1

6-[D-α-(5,6-Benzocoumarin-3-carboxamido)-phenylacetamido]penicillanic acid

To a suspension of 483 mg. of 5,6-benzocoumarin-3-carboxylic acid in 45 ml. of dioxane and 10 ml. of acetone is added 0.282 ml. of triethylamine. The mixture is cooled and stirred in an ice bath and 0.194 ml. of ethyl chloroformate is added dropwise over 10 minutes. Stirring and cooling is continued another 45 minutes. Then 0.281 ml. of triethyl amine and 807 mg. of ampicillin trihydrate are added. Stirring and cooling is continued another hour. A chilled mixture of 3 ml. of saturated sodium bicarbonate solution and 35 ml. of water is added and the reaction mixture is shaken with 100 ml. of ethyl acetate. The mixture is filtered to remove suspended solids. The aqueous layer is acidified, with cooling, with 6 N hydrochloric acid to pH 2 and then extracted with 100 ml., then 50 ml. of ethyl acetate. The combined ethyl acetate extracts are washed with 25 ml. of water, dried over magnesium sulfate and evaporated to a solid. Trituration with ether and filtration gives the desired product, i.r. 5.4μ (β lactam).

EXAMPLE 2

6-[D-α-(5,6-Benzocoumarin-3-carboxamido)-p-hydroxyphenylacetamido]penicillanic acid To a suspension of 483 mg. of 5,6-benzocoumarin-3-carboxylic acid and 0.225 ml. of N-methylmorpholine in 25 ml. of dioxane and 25 ml. of methylene chloride, cooled to −10° to −15° C. in an ice-methanol bath, is added 0.192 ml. of ethyl chloroformate dropwise over several minutes. After an additional 25 minutes of stirring and cooling, 0.223 ml. of N-methylmorpholine and 770 mg. of amoxicillin are added. The mixture is stirred in an ordinary ice bath for one hour. Then a cold mixture of 20 ml. of dioxane, 10 ml. of acetone, 35 ml. of water and 3 ml. of saturated sodium bicarbonate is added. Workup is done as described in Example 1 giving the desired product i.r. 5.65μ (β lactam).

rin-3-carboxamido)-p-hydroxyphenylacetamido]penicillanic acid.

4. A compound of the formula:

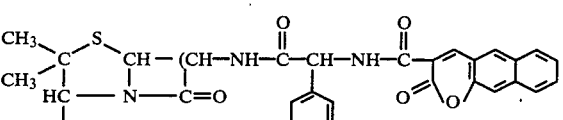

TABLE I

| Compound | Pseudomonas aeruginosa USC 7613 | Klebsiella pneumoniae MA 75-2 | Enterobacter cloacae OSU 75-2 | Proteus mirabills OSU 75-3 | Protues morganii K 72 | Escherichia coli CU 75-1 | Staphylococcus aureus OSU 75-2 |
|---|---|---|---|---|---|---|---|
| 6-]D-α-(5,6-Benzocoumarin-3-carboxamido)phenylacetamido]penicillanic acid | 2 | 16 | 16 | 2 | 32 | 4 | 0.12 |
| 6-[D-α-(5,6-Benzocoumarin-3-carboxamido)-p-hydroxyphenylacetamido]penicillanic acid | 2 | 64 | 64 | 4 | 64 | 16 | 0.5 |
| 6-[D-α-(6,7-Benzocoumarin-3-carboxamido)-phenacid | 1 | 8 | 4 | 0.5 | 16 | 16 | ≦0.06 |
| 6-[D-α-(7,8-Benzocoumarin-3-carboxamido)-phenylacetamido]penicillanic acid | 4 | 16 | 16 | 1 | 16 | 8 | 0.5 |
| Carbenicillin | 32 | >128 | 32 | 1 | 128 | 8 | 0.5 |
| Ampicillin | >128 | 16 | >128 | 0.25 | >128 | 1 | 0.12 |
| 6-[D-α-(7,8-Benzocoumarin-3-carboxamido)-phenylacetamid]penicillanic acid | 2 | 16 | 8 | 4 | 16 | 8 | 0.12 |

EXAMPLE 3

6-[D-α-(6,7-Benzocoumarin-3-carboxamido)-phenylacetamido]penicillanic acid

This compound is prepared similarly to the 5,6-benzo analog of Example 1. Thus, 336 mg. of carboxylic acid [T. Boehm and E. Profft, *Arch. Pharm.*, 269, 25 (1931)] gives the desired compound, i.r. 5.67μ (β lactam).

EXAMPLE 4

6-[D-α-(7,8-Benzocoumarin-3-carboxamido)-phenylacetamido]penicillanic acid

This compound is prepared as described in Example 1, i.r. 5.65μ (β lactam). The acid is prepared after F. D. Cramer and H. Winderl, *Chem. Ber.*, 89, 354 (1956).

We claim:

1. A compound of the formula:

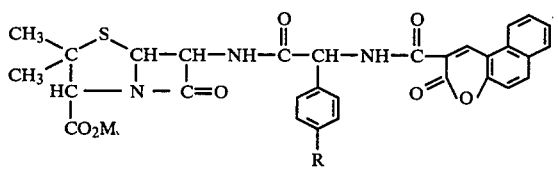

wherein R is hydrogen or hydroxy and M is hydrogen or a pharmacologically acceptable cation.

2. The compound according to claim 1 wherein R and M are both hydrogen; 6-D-α-(5,6-benzocoumarin-3-carboxamido)phenylacetamido]penicillanic acid.

3. The compound according to claim 1 wherein R is hydroxy and M is hydrogen; 6-[D-α-(5,6-benzocoumarin-3-carboxamido)-p-hydroxyphenylacetamido]penicillanic acid.

4. A compound of the formula:

wherein R is hydrogen or hydroxy and M is hydrogen or a pharmaceutically acceptable cation.

5. The compound according to claim 4 wherein R and M are both hydrogen; 6-[D-α-(6,7-benzocoumarin-3-carboxamido)phenylacetamido]penicillanic acid.

6. The compound according to claim 4 wherein R is hydrogen and M is hydrogen; 6-[D-α-(6,7-benzocoumarin-3-carboxamido)-p-hydroxyphenylacetamido]penicillanic acid.

7. A compound of the formula:

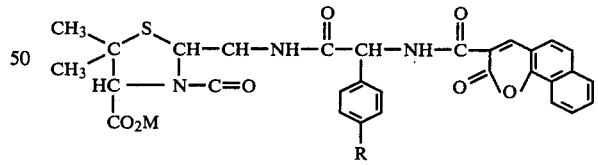

wherein R is hydrogen or hydroxy and M is hydrogen or a pharmacologically acceptable cation.

8. The compound according to claim 7 wherein R and M are both hydrogen; 6-[D-α-(7,8-benzocoumarin-3-carboxamido)phenylacetamido]penicillanic acid.

9. The compound according to claim 7 wherein R is hydroxy and M is hydrogen; 6-[D-α-(7,8-benzocoumarin-3-carboxamido)-p-hydroxyphenylacetamido]penicillanic acid.

* * * * *